(12) United States Patent
Cohen

(10) Patent No.: US 6,929,647 B2
(45) Date of Patent: Aug. 16, 2005

(54) INSTRUMENTATION AND METHOD FOR IMPLANT INSERTION

(75) Inventor: Herb Cohen, Shelton, CT (US)

(73) Assignee: Howmedica Osteonics Corp., Mahwah, NJ (US)

( * ) Notice: Subject to any disclaimer, the term of this patent is extended or adjusted under 35 U.S.C. 154(b) by 182 days.

(21) Appl. No.: 09/789,902

(22) Filed: Feb. 21, 2001

(65) Prior Publication Data

US 2002/0116006 A1 Aug. 22, 2002

(51) Int. Cl.⁷ .................... A61B 17/58; A61B 17/60; A61F 2/00; A61F 2/32; A61F 2/34
(52) U.S. Cl. .................. 606/99; 606/61; 606/79; 606/80; 606/96; 623/11; 623/12; 623/13; 623/14; 623/15; 623/16; 623/17; 623/18; 623/19
(58) Field of Search ............... 606/99, 61, 79, 606/80, 96; 623/17.11, 11, 12, 13, 14, 15, 16, 17, 18, 19

(56) References Cited

U.S. PATENT DOCUMENTS

| | | | |
|---|---|---|---|
| 3,486,505 A | 12/1969 | Morrison | |
| 3,719,186 A | 3/1973 | Merig, Jr. | |
| 3,848,601 A | 11/1974 | Ma et al. | |
| 3,867,932 A | 2/1975 | Huene | |
| 4,347,845 A | * 9/1982 | Mayfield | ............ 128/303 R |
| 4,834,757 A | 5/1989 | Brantigan | |
| 4,877,020 A | 10/1989 | Vich | |
| 4,878,915 A | 11/1989 | Brantigan | |
| 4,961,740 A | 10/1990 | Ray et al. | |
| 5,026,373 A | 6/1991 | Ray et al. | |
| 5,122,130 A | 6/1992 | Keller | |
| 5,431,658 A | 7/1995 | Moskovich | |
| 5,445,639 A | 8/1995 | Kuslich et al. | |
| 5,484,437 A | 1/1996 | Michelson | |
| 5,489,307 A | 2/1996 | Kuslich et al. | |
| 5,505,732 A | 4/1996 | Michelson | |
| 5,554,191 A | * 9/1996 | Lahille et al. | ........... 623/17.11 |
| D374,283 S | 10/1996 | Michelson | |
| 5,562,736 A | 10/1996 | Ray et al. | |
| 5,571,109 A | 11/1996 | Bertagnoli | |
| 5,700,291 A | 12/1997 | Kuslich et al. | |
| 5,720,748 A | 2/1998 | Kuslich et al. | |
| 5,720,751 A | * 2/1998 | Jackson | ....................... 606/86 |

(Continued)

FOREIGN PATENT DOCUMENTS

| | | |
|---|---|---|
| EP | 0 796 593 A | 9/1997 |
| WO | WO 98 17208 A | 4/1998 |
| WO | WO 01 28437 A | 4/2001 |

Primary Examiner—Henry Bennett
Assistant Examiner—Nihir Patel
(74) Attorney, Agent, or Firm—Lerner, David, Littenberg, Krumholz & Mentlik, LLP

(57) ABSTRACT

An implant insertion apparatus for guiding surgical instrumentation and facilitating insertion of surgical implants into an intervertebral space includes an adjustable element defining a longitudinal passageway dimensioned to guide the surgical instrumentation inserted through the longitudinal passageway. The adjustable element has an elongate body and an extended body that are movable relative to one another for varying the length of the adjustable element. The apparatus also includes an engaging element insertable into the intervertebral space between adjacent vertebrae. The engaging element is releasably secured to a distal end of the elongate body.

20 Claims, 14 Drawing Sheets

U.S. PATENT DOCUMENTS

| | | | |
|---|---|---|---|
| D397,436 S | | 8/1998 | Michelson |
| 5,797,909 A | | 8/1998 | Michelson |
| 5,984,967 A | * | 11/1999 | Zdeblick et al. .......... 623/17.16 |
| 6,004,326 A | * | 12/1999 | Castro et al. .................. 606/99 |
| 6,033,405 A | | 3/2000 | Winslow et al. |
| 6,042,582 A | * | 3/2000 | Ray ............................. 606/61 |
| 6,059,790 A | | 5/2000 | Sand et al. |
| 6,063,088 A | * | 5/2000 | Winslow ...................... 606/61 |
| 6,080,155 A | | 6/2000 | Michelson |
| 6,083,225 A | * | 7/2000 | Winslow et al. ............... 606/61 |
| 6,096,038 A | | 8/2000 | Michelson |
| 6,113,602 A | | 9/2000 | Sand |
| 6,120,503 A | | 9/2000 | Michelson |
| 6,159,212 A | * | 12/2000 | Schoedinger et al. .......... 606/61 |
| 6,159,214 A | | 12/2000 | Michelson |
| 6,171,310 B1 | * | 1/2001 | Giordano et al. .............. 606/60 |
| 6,197,033 B1 | * | 3/2001 | Haid et al. ..................... 606/99 |
| 6,224,607 B1 | * | 5/2001 | Michelson ................... 606/96 |
| 6,228,022 B1 | * | 5/2001 | Friesem et al. .............. 600/204 |
| 6,267,763 B1 | * | 7/2001 | Castro ......................... 606/61 |
| 6,428,541 B1 | * | 8/2002 | Boyd et al. .................... 606/61 |
| 6,447,512 B1 | * | 9/2002 | Landry et al. ................. 606/61 |
| 6,478,800 B1 | * | 11/2002 | Fraser et al. ................... 606/99 |
| 6,599,291 B1 | * | 7/2003 | Foley et al. ................... 606/79 |
| 6,635,060 B2 | * | 10/2003 | Hanson et al. ................. 606/79 |
| 6,641,582 B1 | * | 11/2003 | Hanson et al. ................. 606/61 |
| 6,648,895 B2 | * | 11/2003 | Burkus et al. ................. 606/90 |
| 6,663,638 B2 | * | 12/2003 | Ralph et al. ................... 606/99 |
| 6,679,887 B2 | * | 1/2004 | Nicholson et al. ............. 606/84 |
| 6,733,504 B2 | * | 5/2004 | Lin et al. ...................... 606/99 |
| 6,746,454 B2 | * | 6/2004 | Winterbottom et al. ....... 606/99 |
| 6,755,841 B2 | * | 6/2004 | Fraser et al. ................... 606/99 |
| 6,767,354 B2 | * | 7/2004 | Johanson et al. ............ 606/179 |
| 6,767,366 B2 | * | 7/2004 | Lee et al. ................. 623/17.16 |
| 6,790,208 B2 | * | 9/2004 | Oribe et al. ................... 606/53 |

\* cited by examiner

INSTRUMENTATION AND METHOD FOR IMPLANT INSERTION

BACKGROUND

1. Technical Field

The present disclosure generally relates to a method and associated instrumentation for implant insertion and, in particular, to a method and instrumentation for insertion of spinal implants to facilitate fusion of adjacent vertebral bodies.

2. Background of the Related Art

A large number of orthopedic procedures involve the insertion of either natural or prosthetic implants into bone or associated tissues. These procedures include, for example, ligament repair, joint repair or replacement, non-union fractures, facial reconstruction, spinal stabilization and spinal fusion. In a typical procedure, an insert, dowel or screw is inserted into a prepared bore formed in the bone or tissues to facilitate repair and healing. Some implants are particularly configured with cavities and bores to facilitate bony in-growth and enhance anchoring of the implant at the insertion site. Implants in the form of fusion cages having internal cavities to receive bone growth stimulation materials such as bone chips and fragments are disclosed, for example, in U.S. Pat. No. 4,501,269 to Bagby; and U.S. Pat. No. 4,961,740 to Ray et al. These types of implants are particularly well suited for intervertebral spinal fusion procedures necessitated by injury, disease or some degenerative disorder of the spinal disc. Subsequently, there may be progressive degeneration leading to mechanical instability between adjacent vertebrae necessitating direct fusion of the vertebrae while maintaining a pre-defined intervertebral space. This fusion may be accomplished by the insertion of one or more of the specialized implants as discussed above and also discussed in commonly assigned U.S. Pat. No. 5,026,373, the contents of which are incorporated herein by reference.

Both anterior (transabdominal) and posterior surgical approaches are used for interbody fusions of the lumbar spine. Fusions in the cervical area of the spine are primarily performed using a posterior approach. Typically, an implant such as a plug, dowel, prosthesis or cage is inserted into a preformed cavity inside the interbody, interdiscal space. Since it is desirable in these procedures to promote a "bone to bone" bridge, connective tissue and at least a portion of the distal tissue is removed. Preferably, relatively deep cuts are made in the adjacent bones in order to penetrate into the softer, more vascularized cancellous region to facilitate bone growth across the implant.

One of the more critical tasks performed in the insertion of a surgical fusion implant, particularly, in intervertebral spinal fusion, is the formation of the implant receiving cavity or bore between/within the adjacent vertebrae. More particularly, the drilled bore must be equally centered within the intervertebral space and preferably parallel to the vertebral end plates to ensure removal of equal portions of bone from the adjacent vertebrae throughout the length of the cut and subsequent appropriate seating of the implant relative to the vertebral bodies. In addition, the length of the cut by the drill must be accurate depending upon the particular surgical needs for the patient and/or the length of the implant to be inserted.

Surgical instruments for spinal fusion implant insertion are known. Among several instruments, for example, U.S. Pat. No. 6,083,225 to Winslow et al., the contents of which are incorporated herein by reference, discloses an improved type of instrumentation and method for providing optimal alignment for the drilling, tapping and reception of spinal implant. This method uses a particular surgical retractor for inserting into the intervertebral space to distract adjacent vertebrae and performing the surgical procedure with instrumentation inserted through an opening of the surgical retractor.

SUMMARY OF THE INVENTION

The present invention is directed to further improvements in spinal fusion procedures. In accordance with one aspect of the present invention, an improved instrumentation and associated method to facilitate the introduction of fusion implants, which ensures convenient adjustment of the drilling depth for reception of the fusion implants and, if appropriate, for bore tapping procedures, is provided. Another aspect of the present invention is to provide an improved instrumentation and associated method to facilitate the introduction of fusion implants, which further ensures simplified and effective procedures for the implantation of two implants in side-by-side or lateral relation.

In accordance with the present disclosure, an implant insertion apparatus includes a retractor having a longitudinal opening therethrough. The retractor is positionable across an intervertebral space with respect to the adjacent vertebrae to maintain the adjacent vertebrae at a predetermined spaced relation. The insertion apparatus further includes an adjustable element defining a longitudinal passageway for the surgical instrumentation inserted therethrough. The length of the adjustable element is adjustable. Thus, by adjusting the length of the adjustable element, the depth of drilling to form the implant receiving bore within the adjacent vertebrae may be precisely controlled.

The present disclosure is also directed to a method for performing a surgical procedure with the implant insertion apparatus.

BRIEF DESCRIPTION OF THE DRAWINGS

Preferred embodiments of the disclosure are described hereinbelow with reference to the drawings wherein.

DETAILED DESCRIPTION OF THE PREFERRED EMBODIMENT(S)

The preferred embodiments of the method and instrumentation disclosed herein are discussed in terms of orthopedic spinal fusion procedures and instrumentation. It is also envisioned, however, that the disclosure is applicable to a wide variety of procedures including, but, not limited to ligament repair, joint repair or replacement, non-union fractures, facial reconstruction and spinal stabilization. In addition, it is believed that the present method and instrumentation finds application in both open and minimally invasive procedures including endoscopic and arthroscopic procedures wherein access to the surgical site is achieved through a cannula or small incision.

The following discussion includes a description of each instrument utilized in performing a spinal fusion followed by a description of the preferred method for spinal fusion utilizing the instrumentation in accordance with the present disclosure.

In the discussion which follows, the term "proximal", as is traditional, will refer to the portion of the structure which is closer to the operator, while the term "distal" will refer to the portion which is further from the operator.

Figure 1:
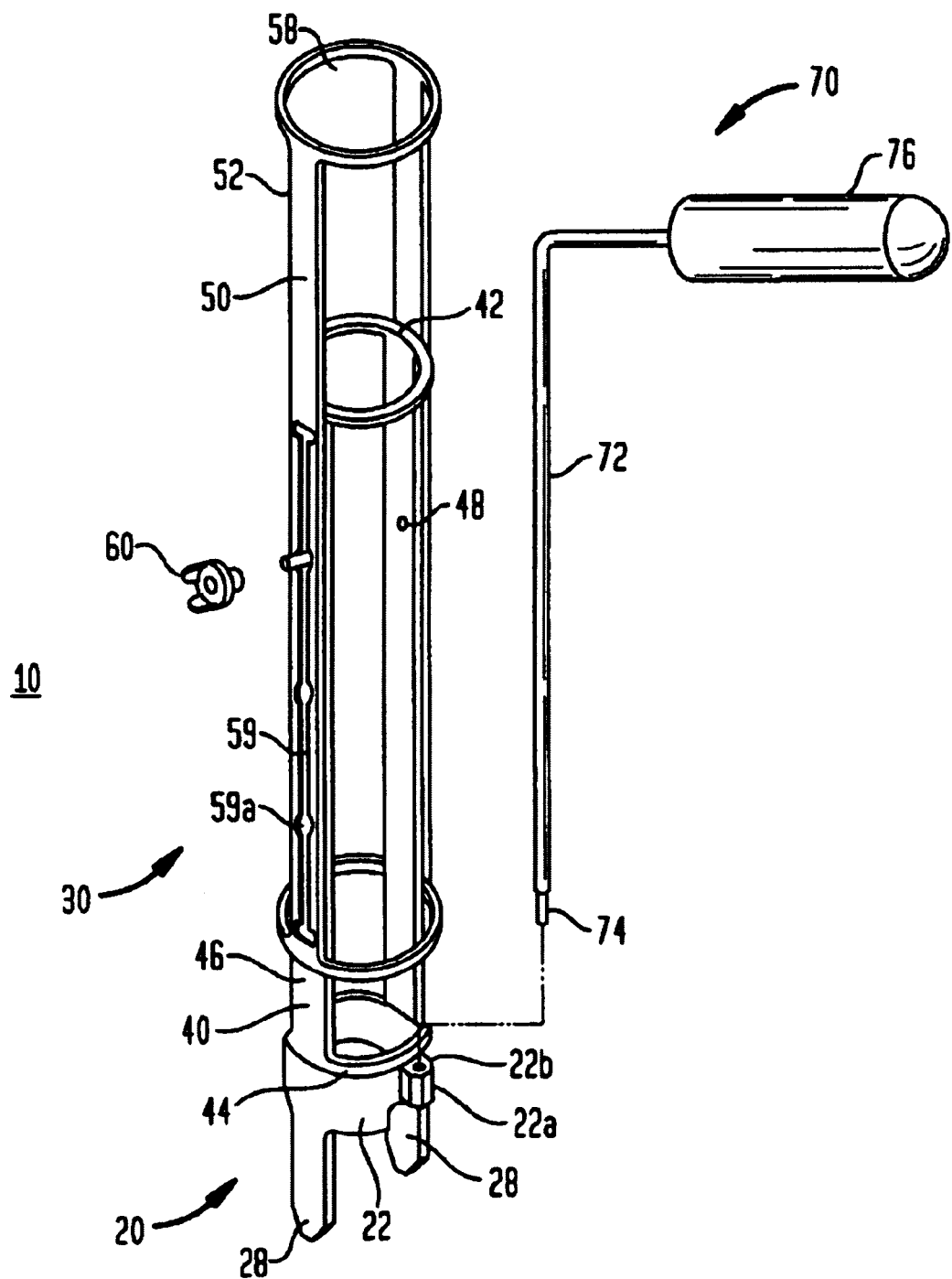
FIG. 1 is a perspective view illustrating an implant insertion apparatus constructed in accordance with one embodiment of the present invention including a retractor, adjustable element and handle.
Figure 2:
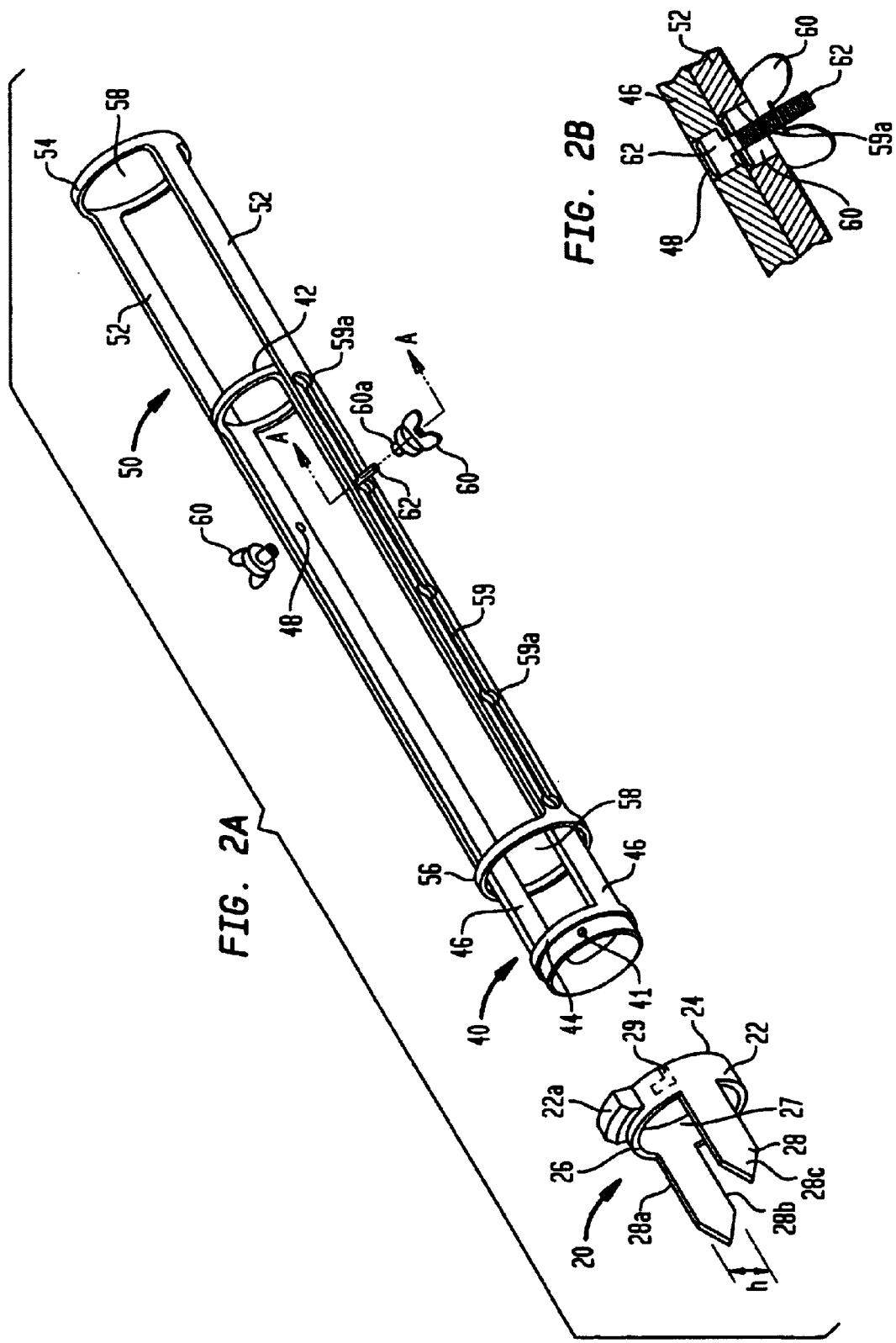
FIG. 2A is a perspective view similar to the view of FIG. 1 illustrating disengaging of retractor from the adjustable element.
FIG. 2B is a partial cross-sectional view of the adjustable element taken along the lines A—A of FIG. 2A, illustrating locking of locking screws to provide length adjustment for the adjustable element.

Referring now to the drawings in which like reference numerals identify similar or identical elements throughout the several views, FIGS. 1–2B illustrate in perspective views an implant insertion apparatus constructed according to the principles of the present disclosure. Implant insertion apparatus 10 includes retractor 20 and adjustable element 30. The adjustable element 30 includes elongate body 40 releasably mounted to the retractor 20, and extended body 50. The insertion apparatus 10 is particularly contemplated for distracting adjacent bony structures, e.g., adjacent opposed vertebral bodies, for providing an opening to facilitate insertion of surgical instrumentation, and for ensuring proper alignment of the instrumentation and accurate insertion of the implant. Although described for spinal procedures, it is envisioned that insertion apparatus 10 may also be utilized to distract other structures as well including joints, ligaments, etc.

Retractor 20 includes base portion 22 having a proximal end portion 24 and a distal end portion 26 and longitudinal opening 27 extending therethrough. Retractor 20 further includes first and second spacer arms 28 extending longitudinally from the distal end 26 of base portion 22. Each spacer arm 28 defines a first vertebra supporting surface 28a to contact a first vertebra and a second vertebra supporting surface 28b to contact a second vertebra with the surfaces 28a and 28b preferably being in general parallel relation to each other. The height "h" of each arm 28 ranges from about 0.3 to 0.4 inches and more preferably from about 0.28 to about 0.35 inches. One skilled in the art will readily appreciate that this dimension can be varied as needed depending upon the procedure. Each arm 28 further includes tapered end portions 28c defining a generally V-shaped configuration. End portions 28c facilitate insertion of the arms 28 within the surgical site, e.g. within the intervertebral space. The retractor 20 further includes a mounting portion 29 in the proximal end 24 of the base portion 22 for mounting the adjustable element 30 as described below.

Referring still to FIGS. 1–2B, the elongate body 40 includes a corresponding mounting portion 41 (FIG. 2A) at its distal end for mounting to the retractor 20. The mounting portion 29 and the corresponding mounting portion 41 may be a bayonet connection of known types (as illustrated), or may be other types of configuration, e.g., a threaded connection. The elongate body 40 includes proximal and distal rims 42, 44, first and second extending portions 46 and at least one screw receiving hole 48 therein.

With continued reference to FIGS. 1–2B, the extended body 50 includes an elongate member 52 and proximal and distal rims 54, 56 defining a longitudinal passageway 58 therethrough for receiving surgical instrumentation described below. The inner diameter of the rims 54, 56 together with the inner surface of the elongate member 52 is preferably dimensioned such that the rim 42 and the extending portions 46 slidably fits therewithin. The extended body 50 further includes at least one positioning groove 59 formed in the elongate member 52. The groove 59 extends along the elongate member 52 and has locking portions 59a to receive locking nuts (described below). The number of the locking portions 59a ranges from 2 to 10, and may be varied depending upon particular surgical needs. The distance between adjacent locking portions ranges from 2 mm to 30 mm, and may also be varied. The elongate member 52 may include length markings (not shown) around the groove 59 for providing indication of relative longitudinal positioning of the extended body 50 with respect to the elongate body 40, and further for determining in advance the ultimate penetrating depth of the surgical instrumentation into the intervertebral space.

The insertion apparatus 10 further includes at least one locking nut 60 for threadably engaging locking screw 62 which is fixedly mounted within the hole 48 of the elongate body 40. The locking nut 60 includes positioning end 60a for engaging the locking portion 59a of the groove 59 to provide the longitudinal positioning of the extended body 50 with respect to the elongate body 40. It should be noted that the extended body 50 is slidably movable along the elongate body 40 when positioning end 60a is disengaged from locking portion 59a. Securement of the locking nut 60 is achieved by threadably advancing the locking nut 60 into position within the locking portion 59a. The overall length from the distal end of the retractor 20 to the proximal end of the extended body 50 is adjustable by locking the locking nut 60 in the locking screw 62 after positioning in the desired location.

Referring still to FIGS. 1–2B, insertion apparatus 10 further includes a retractor handle 70, consisting of a connecting bar 72 with a connecting screw thread 74 at its distal end and a handle 76 at the proximal end of the connecting bar 72. Handle 70 is connected to retractor 20 through threaded connection of screw thread 74 with internal thread disposed within connecting portion 22a of retractor 20. The connecting portion 22a and the retractor handle 70 are provided for aiding manipulation of the retractor 20 or the insertion apparatus 10 for the surgical procedure, as described herein below.

Figure 3:
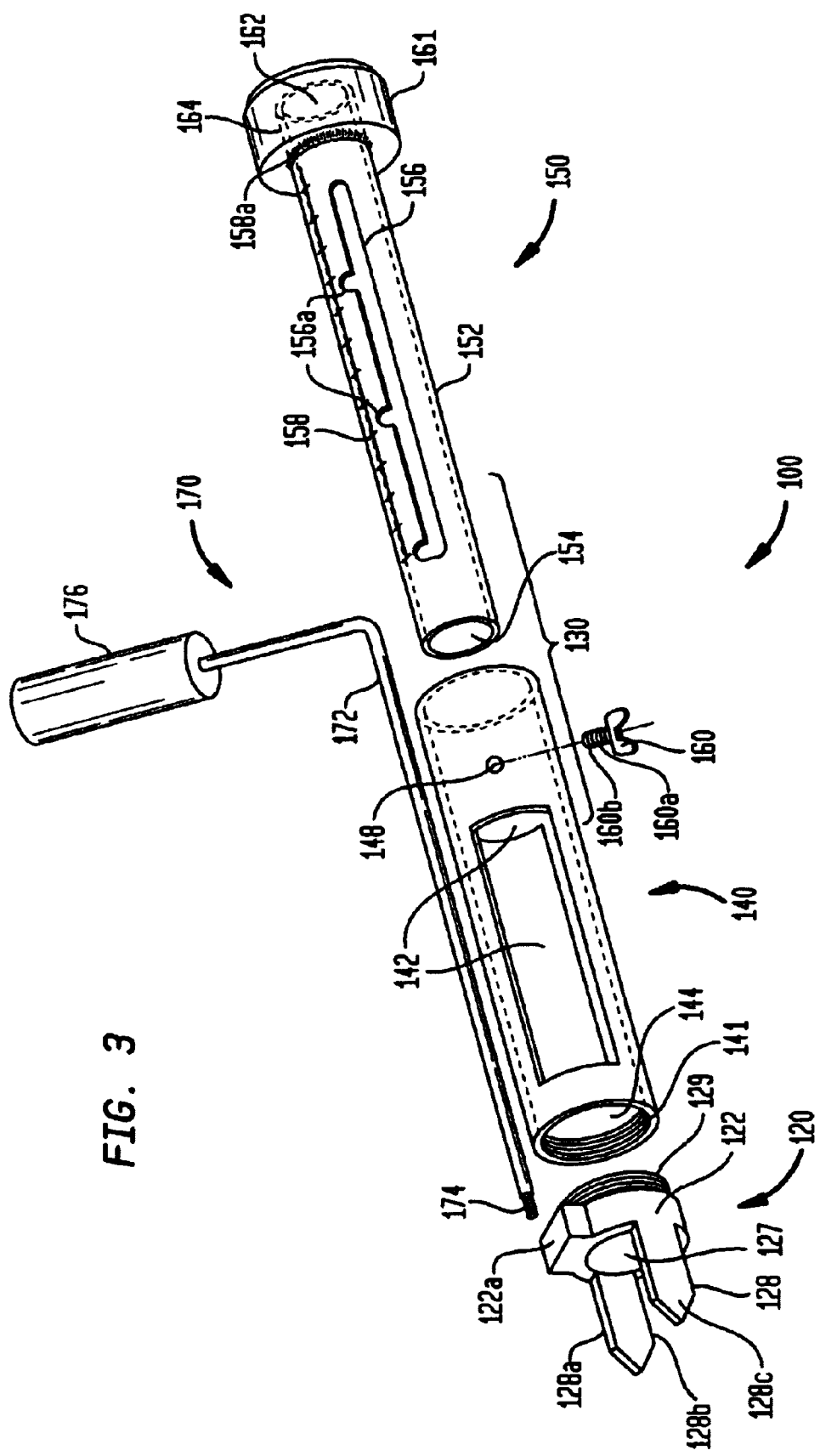
FIG. 3 is a perspective view of an alternate embodiment of the implant insertion apparatus of FIG. 1.
Figure 4:
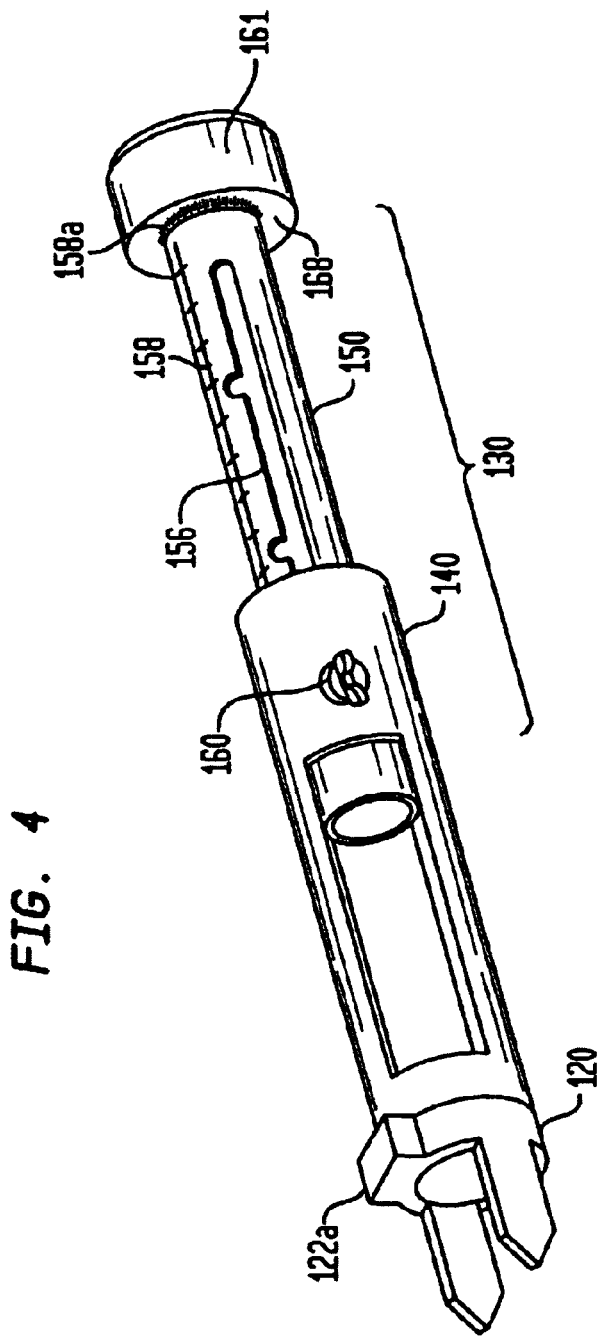
FIG. 4 is a view similar to the view of FIG. 3 illustrating an assembled implant insertion apparatus.

Referring now to FIGS. 3–4, which illustrate an alternative embodiment of the present disclosure, implant insertion apparatus 100 includes retractor 120 and adjustable element 130. The adjustable element 130 includes elongate body 140 releasably mounted to the retractor 120, and extended body 150. Retractor 120 is substantially similar to the retractor 20 discussed in connection with the embodiments of FIGS. 1–2A, but, however includes a threaded portion which facilitates mounting for the adjustable element.

The elongate body 140 includes a corresponding mounting portion 141, i.e., in the form of an internal thread, which threadably receives the threaded portion of retractor 120. The mounting portion 129 and the corresponding mounting portion 141, may be thread-type configurations as shown, or may be other types of configuration, e.g., a bayonet connection. The elongate body 140 may include first and second longitudinally extending openings 142 and at least one screw-receiving threaded hole 148, both the openings 142 and the holes 148 formed in its outer wall. Openings 142 are diametrically arranged with relation to each other. Each opening 142 extends radially for about between 10%–50% the circumference or perimeter of the body 140 and longitudinally for greater than 50% the length of the body 140. Openings 142 are contemplated to permit the lateral introduction of surgical instrumentation required to carry out the fusion procedure as an alternative to introducing the instrumentation through the longitudinal opening 144. These openings 142 also enhance illumination at the surgical site.

Figure 5:
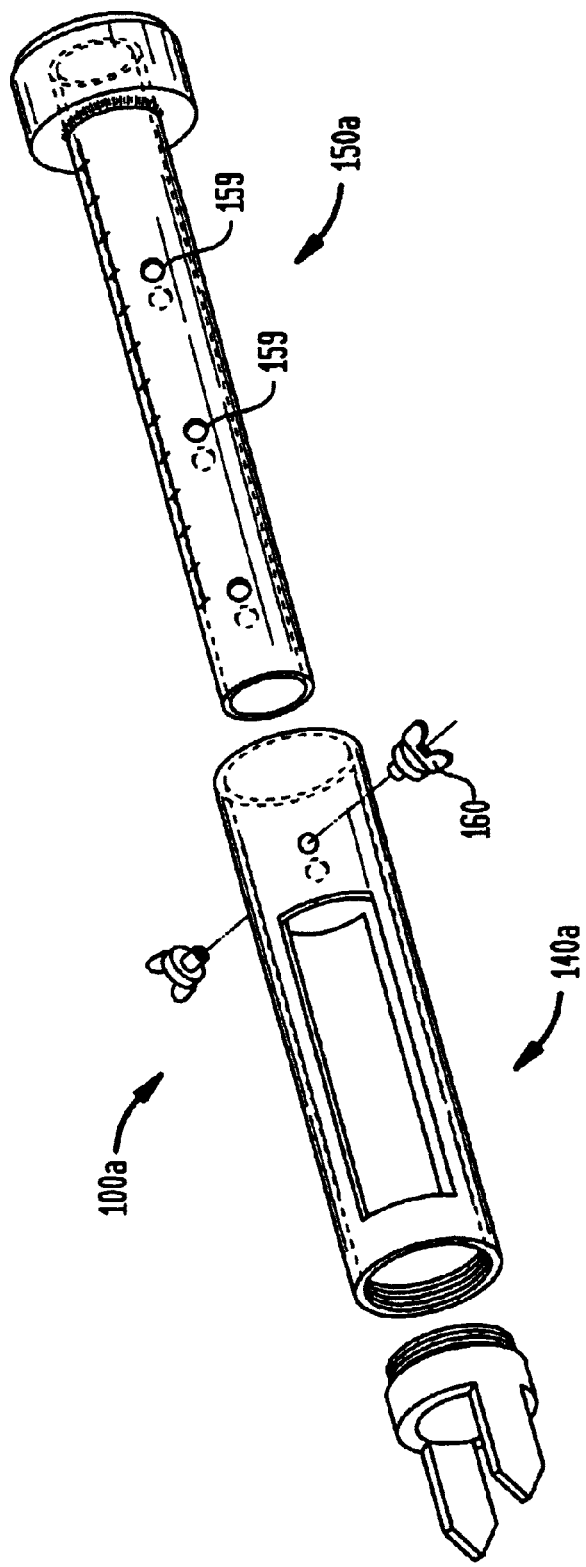
FIG. 5 is a perspective view of another alternate embodiment of the implant insertion apparatus of FIG. 1.

With continued reference to FIGS. 3–4, the extended body 150 includes an elongate member 152 defining a longitudinal passageway 154 therethrough for receiving surgical instrumentation described below. The outer diameter of the member 152 is preferably dimensioned such that the member 152 slidably fits within the opening 144 of the elongate body 140. The extended body 150 further includes at least one positioning groove 156 formed in its outer wall of the member 152. The groove 156 may be complete holes pierced through the wall of the member 152, or may be a groove formed only in the outer surface of the member 152. The grooves 156 may be one extended groove having locking portions 156a (as shown in FIG. 3), or may be multiple separate holes or grooves 159 (as shown in FIG. 5). The number of holes or locking portions ranges from 2 to 10, and may be varied depending upon particular surgical needs. The distance between adjacent holes or locking portions ranges from 2 mm to 30 mm, and may be varied depending upon particular surgical needs. The extended body 150 may include length markings 158 in its outer wall for providing indication of relative longitudinal positioning of the extended body 150 with respect to the elongate body 140, and further for determining in advance the ultimate penetrating depth of the surgical instrumentation into the intervertebral space.

The insertion apparatus 100 further includes at least one locking screw 160 for engaging the screw receiving hole 148 by a threaded portion 160a. The screw 160 includes a positioning end 160b for engaging the groove portion 156 of the extended body 150 to provide the longitudinal positioning of the extended body 150 with respect to the elongate body 140. The overall length from the distal end of the retractor 120 to the proximal end of the extended body 150 is adjustable by locking the screw 160 in the desired locking portion 156a.

The insertion apparatus 100 may further include a head portion 161 connected to the proximal end of the extended body 150 for receiving impact of a driving member for insertion of retractor 120 of the insertion apparatus 100 into the intervertebral space. The head portion 161 includes an opening 162 for receiving the surgical instrumentation. The head portion 161 may be fixedly connected to the extended body 150, or may be longitudinally adjustable with at least a portion of the inner surface of the opening 162 including a threaded portion 164, as it is in the corresponding portion of the extended body 150. An additional longitudinal adjustment may, if needed at all, be performed by turning the head portion 161 with respect to the extended body 150, thus providing a fine adjustment in addition to the primary adjustment made by the screw 160 and grooves 156 as described above. The depth-adjusting process may be further aided by reading the indication of length markings 158. In addition, the head portion 161 may include additional markings 158a in its distal facing surface 168. The penetrating depth may be finely adjusted by turning back or forth the head 161 around the extended body 150 while reading the additional markings 158a or reading the length markings 158.

Referring now to FIG. 5, which illustrates another alternative embodiment of the present disclosure and is in similar structure to the embodiment described with FIGS. 3–4, extended body 150a may include, as an alternative to the groove 156, a plurality of holes 159 for receiving the screw 160 to adjust the depth of the adjustable element 130. The number of the holes may be varied depending upon the particular surgical needs.

Figure 6:
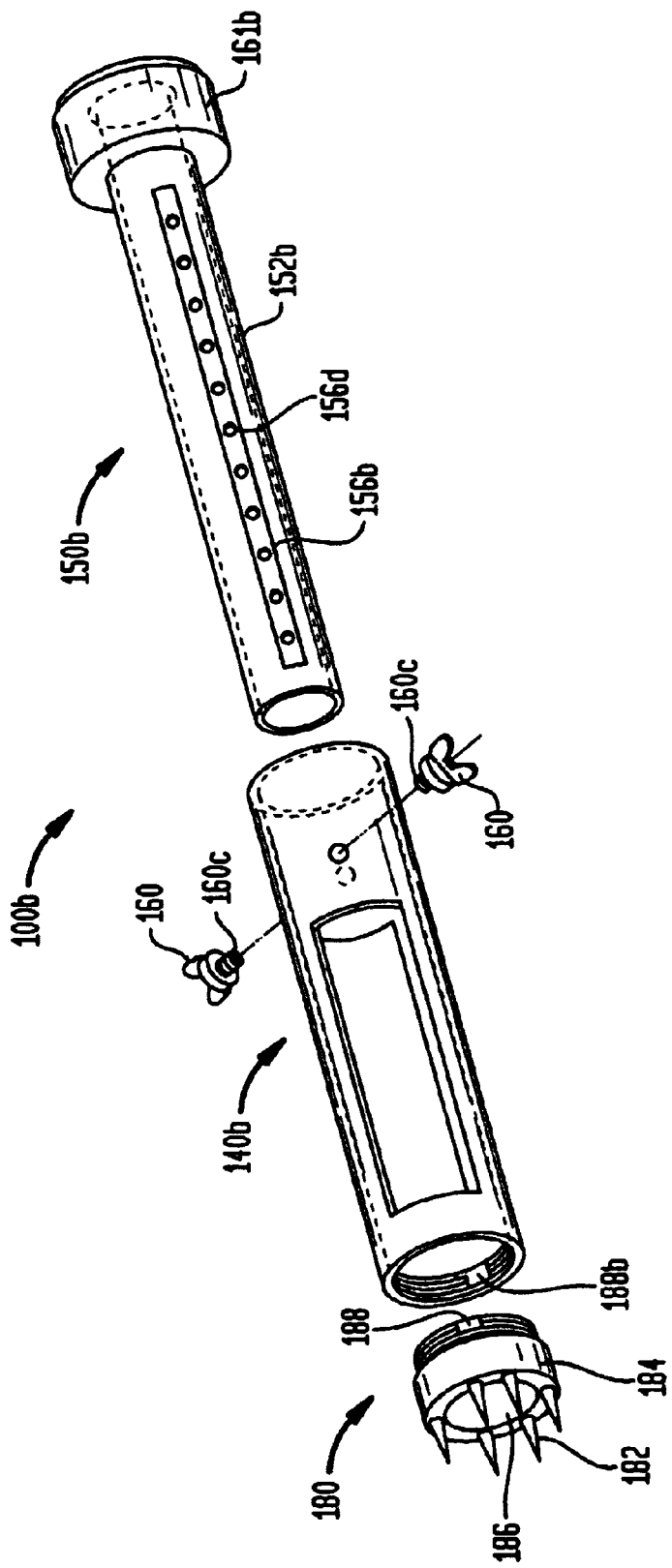
FIG. 6 is a perspective view of another alternate embodiment of the implant insertion apparatus of FIG. 1.

Referring now to FIG. 6, which illustrates another alternative embodiment of the present disclosure, the insertion apparatus 100b includes, as an alternative to the retractor 20 or 120 in FIGS. 1–5, an engaging member 180 having tacks 182 for inserting and mounting to the tissue, e.g., adjacent vertebrae across an intervertebral space. The number and size of the tacks may be varied depending upon the particular surgical needs. The engaging member 180 includes a base portion 184 having a proximal end portion and a distal end portion. The base portion 184 includes a longitudinal opening 186 therethrough between the proximal end and the distal end of the base portion 184. The engaging member 180 further includes a bayonet-type mounting portion 188 in the proximal end of the base portion 184. The insertion apparatus 100b further includes an elongate body having a corresponding mounting portion 188b in its distal end. As described above such mounting may be achieved by other types of releasable connection, e.g., thread-type connection. The elongate body 140b may be in a similar structure as described above with FIGS. 3–4.

Referring still to FIG. 6, the insertion apparatus 100b further includes extended body 150b having similar structure described above. The extended body 150b includes at least one groove 156b formed in the outer surface of the member 152b, i.e., the groove being built without piercing through the wall of the member 152b. By locking the screw 160 onto the groove 156b, length adjustment can be achieved in any longitudinal positions along the length of the groove 156b. The adjustable element may alternatively include positioning dents 156d formed along in the groove 156b to receiving the distal tip 160c of the screw 160 and getting multiple predetermined positioning.

Figure 7:
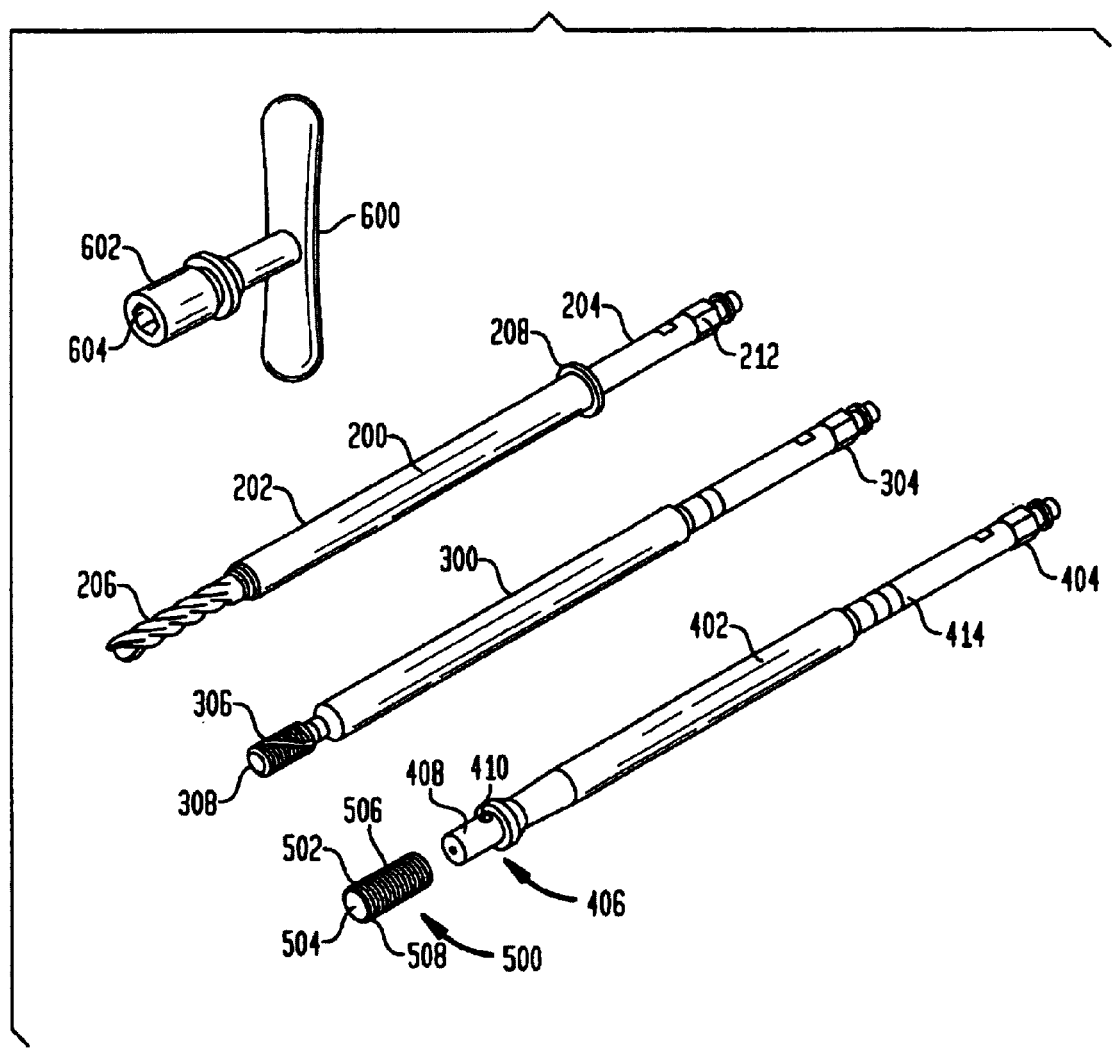
FIG. 7 is a perspective view of a surgical kit utilized for insertion of a fusion implant including, from bottom to top, an implant insertion instrument and fusion implant, a tap instrument, a drill instrument and a T-shaped handle.

Referring now to FIG. 7, the various other instruments contemplated for use in the spinal fusion procedure are illustrated, including surgical drill 200, surgical tap instrument 300, implant insertion instrument 400 with implant 500 and T-shaped handle 600. Drill instrument 200 includes drill shaft 202, extension shaft 204 and drill bit 206 mounted at the distal end of the drill shaft. Extension shaft 204 has a collar 208 to control, together with the insertion apparatus 10, the depth of penetration of drill shaft 202 and drill bit 206 into adjacent vertebrae. Drill shaft 202 includes a hexagonal-shaped head 212 at its proximal end to mount T-handle 600.

Tap instrument 200 is disclosed in the Winslow '225 patent mentioned above. Tap instrument 300 is utilized for performing an internal thread within the drilled bore formed by the drill instrument. Tap instrument 300 includes elongated member 302 having hex head 304 at its proximal end to engage T-shaped handle 600. Tap instrument 300 further includes distal tapping threaded portion 306. Distal tapping portion 306 includes a plurality of conveyance channels (one is shown) 308 extending longitudinally through the cutting thread. Each conveyance channel 308 has a directional component parallel to the longitudinal axis and a directional component transverse to the longitudinal axis. Each conveyance channel 308 encompasses approximately an arc of about ⅓ the outer circumference of the tapping portion 306. Conveyance channels 308 are each dimensioned to receive bone material deburred by the cutting edges during the tapping procedure and to continually transmit the bone material proximally through the channel to avoid undesired material build up at the tapping site. In this manner, tapping instrument 300 may be used to completely tap the internal thread within the bore without interruption of the tapping procedure.

Implant insertion instrument 400 is also disclosed in the Winslow '225 patent. It should be noted that the tap need not be used if a self-tapping implant is utilized. Implant insertion instrument 400 includes elongated member 402 having proximal mounting portion 404 to engage T-shaped handle 600 and distal portion 406 which mounts implant 500. Distal portion 406 includes cylindrical mount 408 which is received within the bore of the implant 500 and implant engaging ball 410 which is received within an aperture defined in the wall of the implant 500 to positively fix the implant to the instrument A hand lever 412 is proximally located and is operatively connected to an inner drive member (not shown) disposed within elongated member 402. The hand lever 412 is longitudinally movable to translate the drive member which, in turn, moves through a camming action implant engaging in ball 410 between an outward position in engagement with the implant 500 and an inward position released from the implant 500.

Implant 500 is uniquely designed for use in spinal fusion procedures. This implant 500 is generally disclosed in U.S. Pat. No. 5,026,373 to Ray, the contents of which have been previously incorporated herein by reference, and is commonly referred to as a "fusion cage". Implant or fusion cage 500 includes a cylindrical cage body 502 having an internal cavity or hole for accommodating bone-growth inducing substances. One end 504 of cage body 502 is closed and defines a rounded or bull-nosed configuration to facilitate insertion of the fusion cage relative to one or more bony structures. The other end defines an opening which communicates with the internal cavity. The outer surface of the cage body 502 includes a single continuous thread 506 (preferably V-shaped) having a plurality of raised turns with valleys defined between adjacent turns.

A plurality of perforations 508 are disposed within the threads and extend through the outer surface of the cage body 502 to provide direct communication between the outer surface and internal cavity 504. The perforations 508 permit immediate contact between the bone growth inducing substances within the inner cavity and the bone structure when the cage body 502 is mated to the bone structure, e.g., adjacent vertebrae. An end cap (not shown) may be mountable to the open end of cage body 502 to enclose the bone-growth inducing substances within the interior cavity.

T-shaped handle 600 includes mounting portion 602 defining hexagonal-shaped recess 604 which receives the corresponding structure of drill instrument 200, tap instrument 300 and implant insertion instrument 400.

Application of Instrumentation

The use of the instrumentation in conjunction with the insertion of the fusion cage 500 into an intervertebral space defined between adjacent vertebrae will be described. The subsequent description will be particularly focused on an open posterior spinal fusion procedure, using two implants in side-by-side relation. However, it is to be appreciated that an anterior approach or a singular implant insertion approach is contemplated as well.

Figure 8:
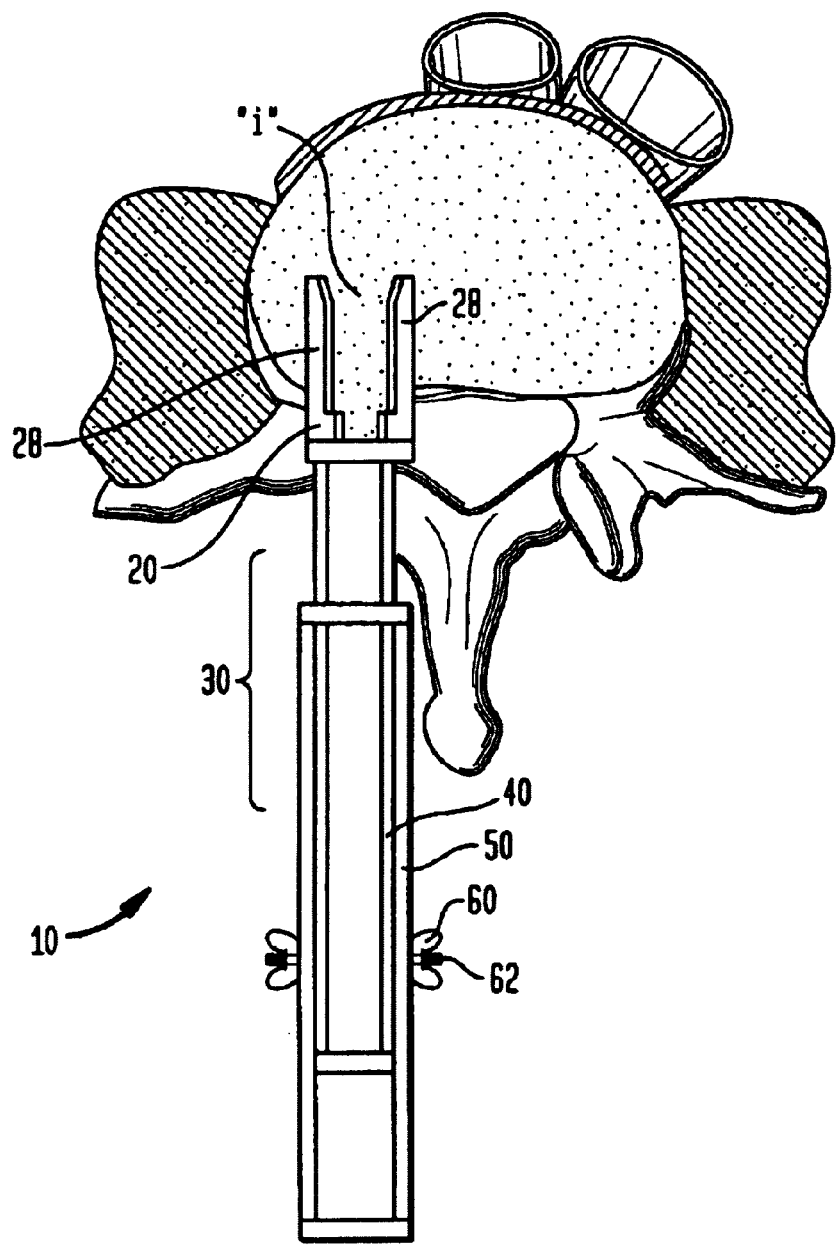
FIG. 8 is a top cross-sectional view of an intervertebral space defined between adjacent vertebrae illustrating insertion of the implant insertion apparatus of the present disclosure.
Figure 9:
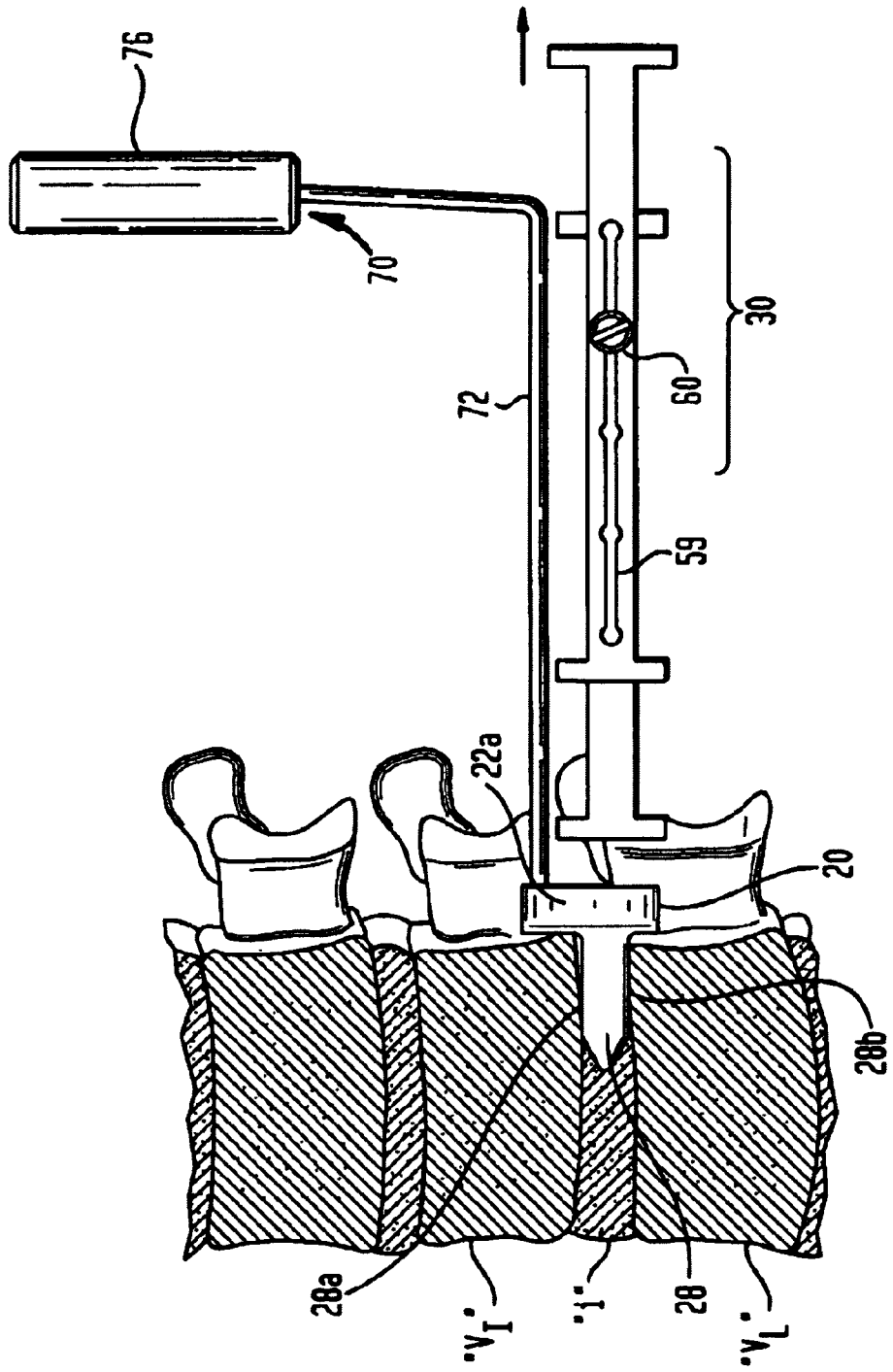
FIG. 9 is a side cross-sectional view of the vertebral column further illustrating positioning of the implant insertion apparatus having a handle connected to the retractor, in accordance with the principles of the present disclosure.

The intervertebral space is accessed utilizing appropriate instrumentation to expose the posterior vertebral surface. Then, the desired-sized vertebral retractor 20, or engaging member 180, is selected and mounted to the adjustable element 30 by cooperation of corresponding mounting portions 29, 41 (FIG. 2A) of the retractor and the elongate body 40. With reference to FIG. 8, a first lateral side of the intervertebral space "i" is targeted. By manipulating the insertion apparatus 10, spacer arms 28 of the retractor 20 is inserted within the intervertebral space "i" adjacent the first lateral side. A standard mallet may be utilized to impact the proximal end of the apparatus 10, or alternatively elongate body 30, to drive spacer arms 28 into the disc space. Spacer arms 28 are inserted in a manner such that first and second supporting surfaces 28a, 28b of each spacer arm 28 respectively engage the opposed vertebral bodies "$v_1$ $v_2$" as depicted in FIG. 9. Once in position, the adjustable element 30 is removed from the retractor 20 by rotating to disengage the respective mounting portions 29, 41 thereby leaving the retractor 20 within the intervertebral space. As shown in FIG. 9, the retractor 20 may include connecting portion 22a (shown the details in FIG. 1), and the insertion apparatus 10 may further include a retractor handle 70 releasably connected to the connecting portion 22a. By holding the retractor handle, the removal of the adjustable element 30 may be further secured without dislodging or harmful movement in any direction. Thereafter, the retractor handle 70 may also be removed from the retractor 20. The spacer arms 28 of retractor 20 are appropriately dimensioned to stabilize the desired lateral side of the intervertebral space. It is to be noted that retractor 20 may distract the adjacent vertebrae "$v_1$ $v_2$" as desired to become firmly implanted within the intervertebral space "i".

Figure 10:
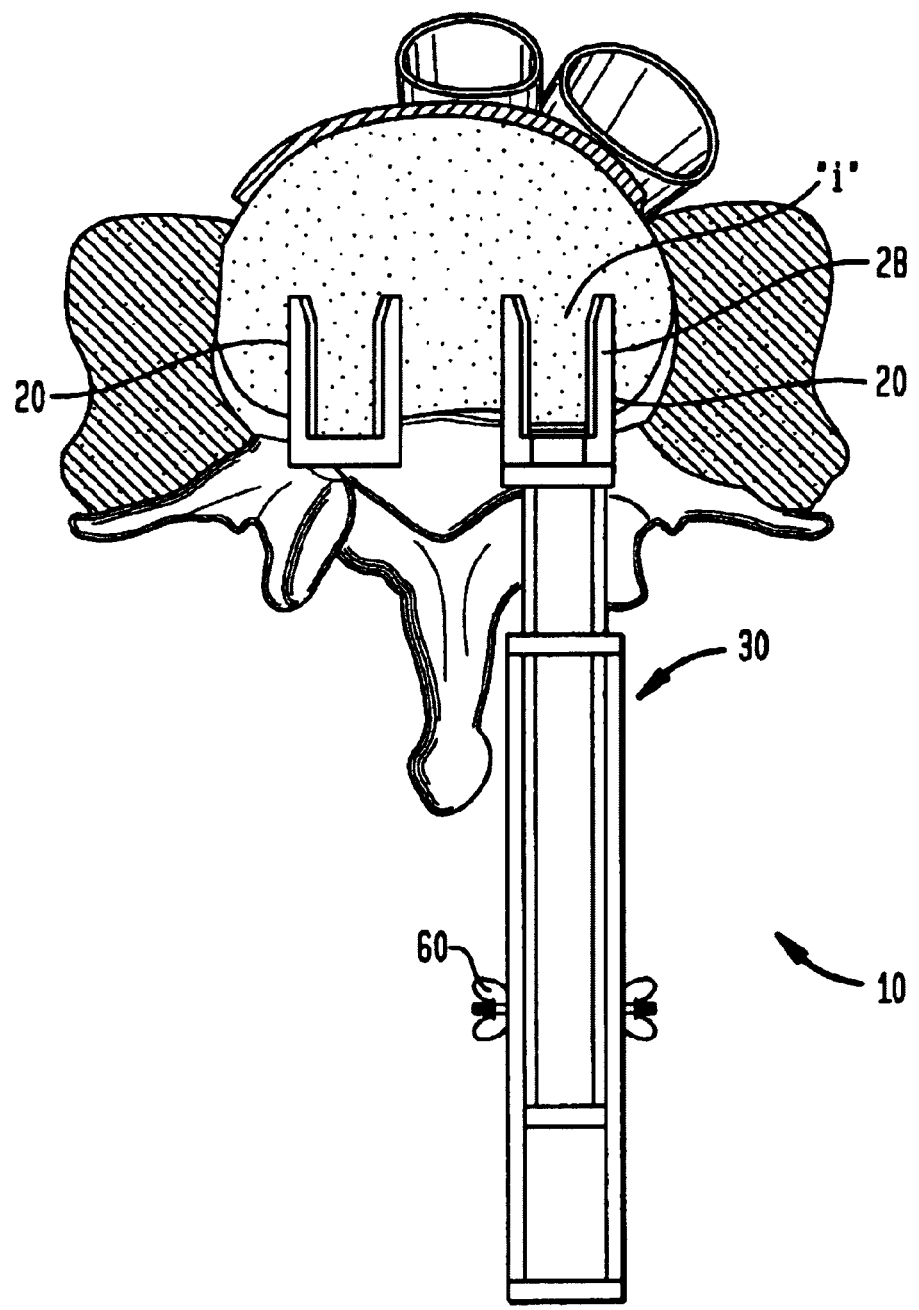
FIG. 10 is a view similar to the view of FIG. 8 illustrating positioning of the retractor in one lateral side of the intervertebral space and insertion of an implant insertion apparatus in the other lateral side of the space.

With reference now to FIG. 10, insertion apparatus 10 including another retractor 20 is likewise inserted within the intervertebral space "i" adjacent the other lateral side thereof. The apparatus 10 may be inserted by impacting the proximal end of the apparatus 10 into the intervertebral space "i". Upon insertion of spacer arms 28, the vertebral bodies "$v_1$ $v_2$" are distracted whereby the arms 28 become firmly lodged within the intervertebral space. The retractor 20 selected preferably corresponds in dimension to the first retractor 20 to ensure parallel distraction of the adjacent vertebrae "$v_1$ $v_2$" so as to maintain a predetermined spacial distance of the vertebrae across the span of the intervertebral space "i".

Figure 11:
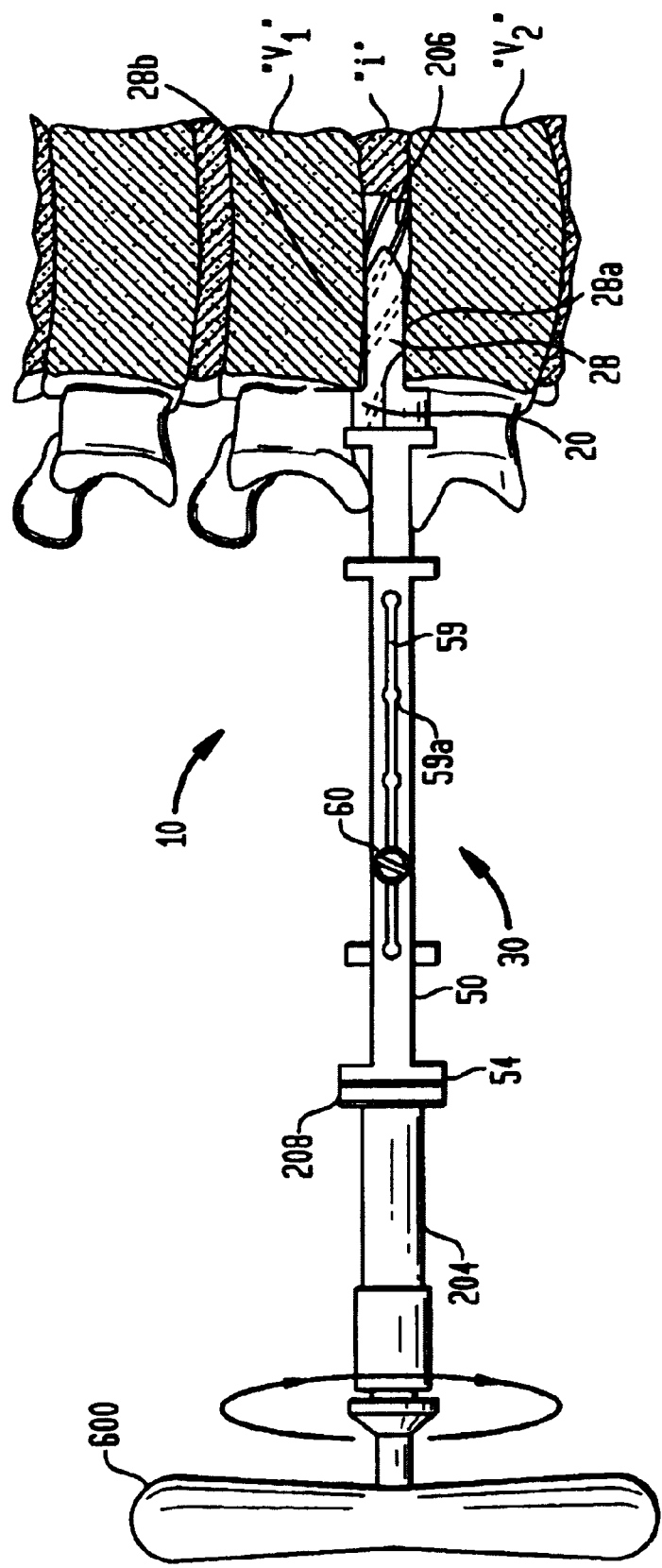
FIG. 11 is a view similar to the view of FIG. 9 illustrating insertion of the drill instrument into the implant insertion apparatus to drill a bore within the adjacent vertebrae.

Referring now to FIG. 11, the surgical drill instrument 200 is now utilized to prepare the disc space and vertebral end plates for insertion of the fusion implant. The cutting depth of drilling is adjusted in advance as desired by utilizing the telescopic length-adjusting features of the present invention: i.e., first, the overall length of the adjustable element 30 is set by positioning distal end portion of the screw 62 into an appropriate locking portion 59a of the groove 59; then, locking nut 60 is advanced until positioning end 60a (FIG. 2B) securely engages locking portion 59a of the groove 59. It should be noted that the depth adjustment utilizing the element 30 may be alternatively performed before insertion of the apparatus 10 into the intervertebral space. Now, with the T-handle mounted to surgical drill instrument 200, the instrument is introduced into the axial bore of retractor 20 and advanced to contact the posterior surface of the vertebral bodies, "$v_1 v_2$". Drill 200 is advanced into the intervertebral space "i" by rotating T-handle 600 such that drill bit 200 shears the soft tissue and cuts the bone of the adjacent vertebrae "$v_1 v_2$" thereby forming a bore which extends into the adjacent vertebrae "$v_1 v_2$" until stopping collar 208 contacts the proximal end surface of rim 54. Drill 200 is then removed from insertion apparatus 10. It is to be noted that during the bore forming process, the pre-inserted retractor 20 in conjunction with the current retractor 20 stabilize the adjacent vertebrae "$v_1 v_2$" (e.g., the first and second lateral sides of the intervertebral space are stabilized by retractor arms 28 of the two retractors 20) to minimize lateral and/or longitudinal movement of the bodies and also to facilitate the formation of a uniform bore within the end plates.

Figure 12:
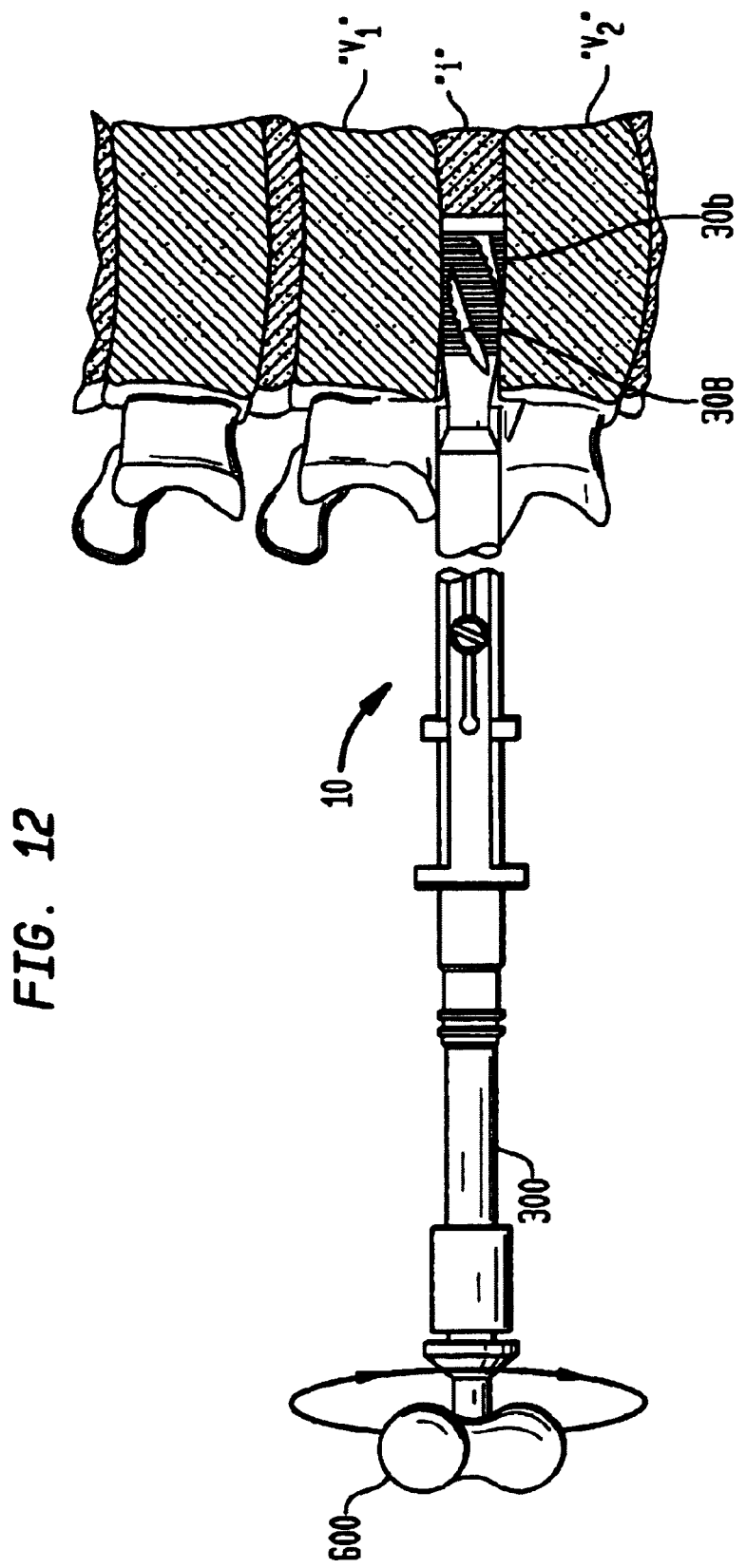
FIG. 12 is a view similar to the view of FIG. 11 illustrating insertion of the tap instrument into the implant insertion apparatus to tap the bore formed by the drill instrument.

Referring now to FIG. 12, tap instrument 300 is selected and attached to the T-handle 600. Tap instrument 300 is inserted into insertion apparatus 10 and positioned adjacent the drilled bore formed in the adjacent vertebrae "$v_1 v_2$" by the surgical drill 200. With insertion apparatus 10 as a direct guide, T-handle 600 is rotated in the direction of the directional arrow of FIG. 12 while simultaneously applying sufficient downward pressure on the T-handle to advance the tap instrument 300 and promote even purchase into the endplates. Upon advancement of the tap instrument 300, the deburred bone chips collect within conveyance channel 308 of tapping head 306, and are conveyed proximally during rotational movement of the tapping head away from the tapping site. Tap instrument 300 is advanced into the bone until the desired depth has been achieved, which occurs when the distal end of tapping head 308 "bottoms out" on the bone. When tap instrument 300 reaches the appropriate depth, the tap instrument 300 is rotated via T-handle 600 in an opposite direction to back the instrument out of the bone.

With reference now back to FIG. 9, adjustable element 30 is removed from the retractor 20 by disengaging the respective mounting portions 29, 41 thereby leaving the retractor 20 within the intervertebral space. The removal of the adjustable guide from the retractor may be further secured by holding retractor handle 70.

Figure 13:
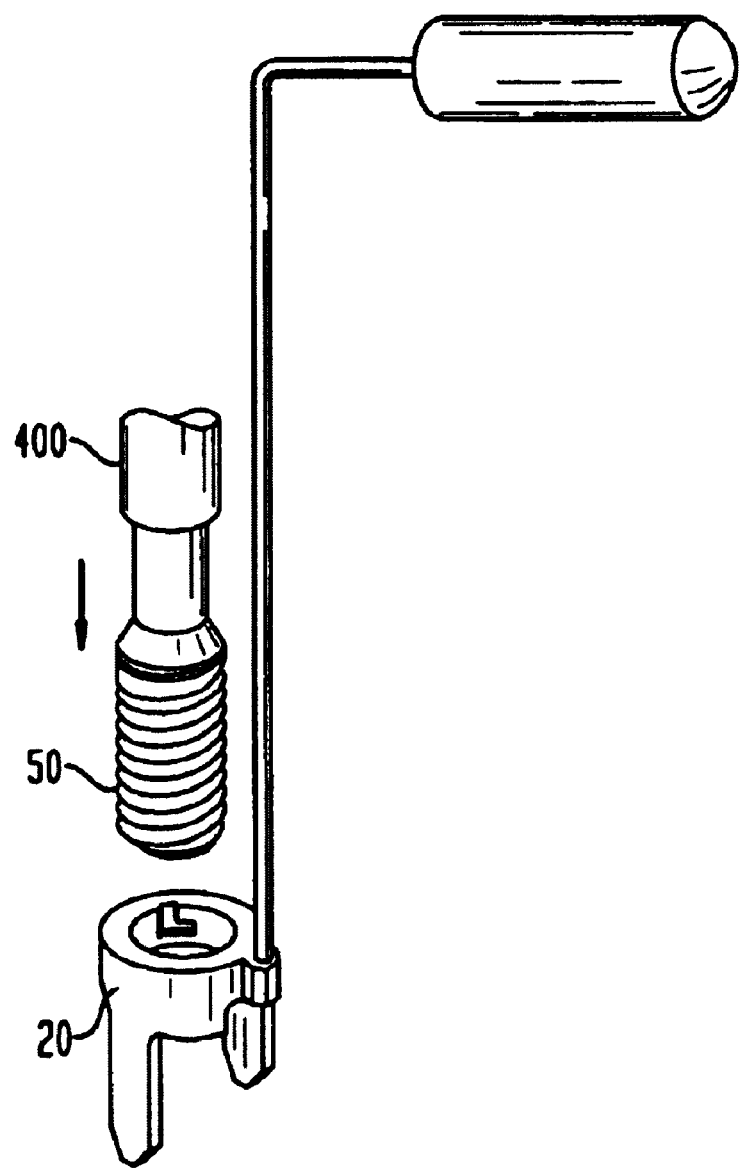
FIG. 13 is a perspective view illustrating insertion of the implant insertion instrument with mounted implant into the retractor to insert the implant.

With reference now to FIG. 13, attention is focused on the insertion of fusion implant 500. Cage body 502 is mounted onto insertion instrument 400 by positioning the cage body 502 onto mounting portion 408 of the instrument to permit mounting ball 410 to engage one of the apertures of the implant 500. This assembly is attached to T-handle 600. Insertion instrument 400 with mounted cage body 502 is inserted into the retractor 20 and the cage body 502 is positioned within the tapped bore by rotating insertion instrument 400 in the appropriate direction. Cage body 502 is advanced until it is completely seated with the bore. An indicator line 414 (FIG. 7) on insertion instrument 400 assists the surgeon in determining when the cage is in proper position. Insertion instrument 400 is then removed from retractor 20.

At this point in the procedure, bone growth inducing substances may be harvested from, e.g., the iliac crest, and packed into the cage body 502 of implant 500 until the cage body 502 is completely filled with bone growth inducing substances. An end cap may then be mounted to the cage body 202. Retractor 20 is then removed by manipulating the retractor handle 70.

With implant 500 appropriately positioned in the second lateral side of the intervertebral space "i", attention is directed to preparing the first lateral side for insertion of a second implant. Adjustable element 30 is now mounted to the previously inserted retractor 20 in the same manner described above.

A second bore is formed in this first lateral side with drilling and tapping, if desired, followed by insertion of the implant as effectuated in accordance with the methods and instruments described above in connection with FIGS. 7–13.

Figure 14:
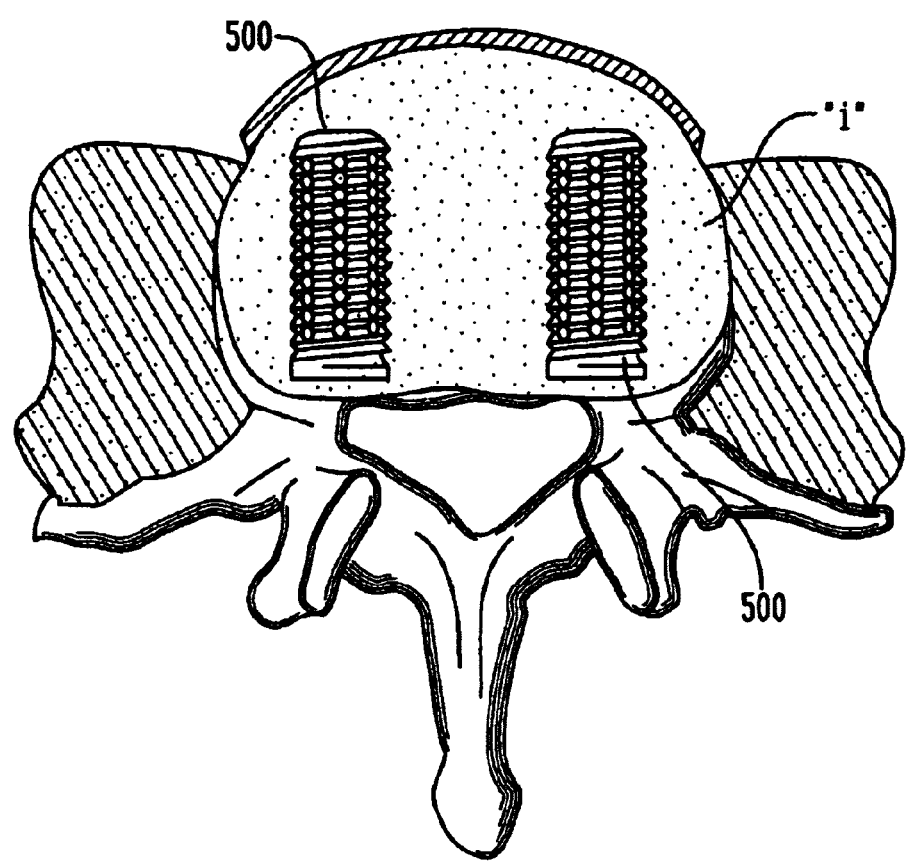
FIG. 14 is a view illustrating insertion of a pair of fusion implants into the intervertebral space.

FIG. 14 illustrates two lateral fusion implants 500 inserted within the intervertebral space.

While the above description contains many specifics, these specifics should not be construed as limitations on the scope of the disclosure, but merely as exemplifications of preferred embodiments thereof. For example, it is envisioned that a self-tapping implant may be utilized thus precluding the use of tap instrument 300. Those skilled in the art will envision many other possible variations that are within the scope and spirit of the disclosure as defined by the claims appended hereto.

What is claimed is:

1. An implant insertion apparatus for guiding surgical instrumentation and facilitating insertion of surgical implants into an intervertebral space comprising:

an adjustable element having a proximal end and a distal end, the adjustable element defining a longitudinal passageway extending from the proximal end to the distal end that is dimensioned to guide the surgical instrumentation inserted through the longitudinal passageway, the adjustable element including an elongate body and an extended body that are movable relative to one another for varying the length of the adjustable element; and an engaging element insertable into the intervertebral space between adjacent vertebrae, wherein the engaging element is releasably secured to the distal end of the elongate body.

2. The implant insertion apparatus according to claim 1 further including positioning members for setting relative positions of the extended body with respect to the elongate body to adjust the length of the adjustable element.

3. The implant insertion apparatus according to claim 2 wherein the positioning members includes at least one positioning groove in the adjustable element and a locking element to engage the positioning groove.

4. The implant insertion apparatus according to claim 1 wherein the engaging element includes a base having a proximal end and a distal end, and defining a longitudinal opening therethrough.

5. The implant insertion apparatus according to claim 4 wherein the engaging element further includes first and second spacer arms extending longitudinally from the distal end of the base, each spacer arm defining a first vertebra supporting surface to contact a first vertebra and a second vertebra supporting surface to contact a second vertebra.

6. The implant insertion apparatus according to claim 1 wherein the engaging element is releasably secured to the distal end of elongate body of the adjustable element by a bayonet-type connection.

7. The implant insertion apparatus according to claim 1 further including a handle mounted to the engaging element.

8. The implant insertion apparatus according to claim 1 further including a head mounted to a proximal end of the extended body of the adjustable element, the head having a greater cross-sectional dimension than the engaging element for receiving impact of a driving member for positioning the engaging element with respect to the adjacent vertebrae.

9. The implant insertion apparatus according to claim 8 wherein the head is longitudinally adjustably mounted to the adjustable element and includes an opening for receiving the surgical instrumentation.

10. A method for performing a surgical procedure comprising the steps of:

providing an adjustable element having a proximal end and a distal end, the adjustable element defining a longitudinal passageway extending from the proximal end to the distal end for receiving surgical instrumentation, the adjustable element including an elongate body and an extended body that are movable relative to one another for varying the length of the adjustable element;

moving the elongate body relative to the extended body for adjusting the length of the adjustable element;

providing an engaging element adapted for insertion into an intervertebral space between adjacent vertebrae and releasably securing the engaging element to the distal end of the elongate body;

after releasably securing the engaging element to the distal end of the elongate body, inserting the engaging element into the intervertebral space for maintaining the adjacent vertebrae in predetermined spaced relation; and introducing the surgical instrumentation within the longitudinal passageway of the adjustable element to perform a surgical procedure.

11. The method according to claim 10 wherein the step of introducing includes advancing a surgical drill through the longitudinal passageway of the adjustable element to drill a bore between the adjacent vertebrae whereby the depth of advancement of the drill is controlled by the length of the adjustable element.

12. The method according to claim 11 further including the step of releasing the engaging element from the adjustable element.

13. The method according to claim 12 wherein the engaging element has a longitudinal opening extending therethrough and wherein the step of introducing includes advancing a surgical implant through the longitudinal opening of the engaging element and into the bore between the adjacent vertebrae.

14. A method for performing a procedure for implantation of at least two implants in side-by-side relation, comprising the steps of:

providing first and second engaging elements insertable in side-by-side relation in an intervertebral space between adjacent vertebrae, each engaging element defining a longitudinal opening therethrough;

providing an elongate member defining a longitudinal passageway for receiving surgical instrumentation, wherein the length of the elongate member is variable;

securing the first engaging element to the elongate member;

positioning the first engaging element into the intervertebral space between the adjacent vertebrae;

releasing the elongate member from the first engaging element thereby leaving the first engaging element within the intervertebral space;

after releasing the elongate member from the first engaging element, securing the second engaging element to the elongate member;

positioning the second engaging element into the intervertebral space between the adjacent vertebrae wherein the first and second engaging elements are in a side-by-side relation to one another in the intervertebral space; and performing the surgical procedure at the intervertebral space.

15. The method for performing a surgical procedure according to claim 14, wherein the method further includes the step of adjusting the length of the elongate member.

16. The method for performing a surgical procedure according to claim 14 further comprising the step of:

performing the surgical procedure at the intervertebral space when the first engaging member is secured to the elongate member.

17. The method for performing a surgical procedure according to claim 14 wherein the engaging element further includes a handle releasably mounted thereto, the method further comprising holding the handle mounted to the engaging element.

18. The implant insertion apparatus as claimed in claim 4, wherein the elongate body includes a rim at the distal end thereof adapted to be coupled with the base of the engaging element.

19. The implant insertion apparatus as claimed in claim 1, further comprising:

the elongate body having proximal and distal rims and first and second extending portions that extend between the proximal and distal rims;

the extended body having proximal and distal rims and first and second supporting elements that extend between the proximal and distal rims of the extended body, wherein the diameter of the proximal and distal rims of the elongate body is less than the diameter of the proximal and distal rims of the extended body so that the elongate body slidably fits within the extended body.

20. The implant insertion apparatus as claimed in claim 1, wherein the elongate body defines a first diameter and the extended body defines a second diameter, the first diameter being less than the second diameter so that the elongate body may slidably fit within the extended body.

* * * * *

UNITED STATES PATENT AND TRADEMARK OFFICE
CERTIFICATE OF CORRECTION

PATENT NO. : 6,929,647 B2
DATED : August 16, 2005
INVENTOR(S) : Herb Cohen

It is certified that error appears in the above-identified patent and that said Letters Patent is hereby corrected as shown below:

Column 11,
Line 1, insert the word -- the -- before the word "elongate".

Signed and Sealed this

Twenty-second Day of November, 2005

JON W. DUDAS
*Director of the United States Patent and Trademark Office*